(12) United States Patent
Dai et al.

(10) Patent No.: US 6,229,054 B1
(45) Date of Patent: May 8, 2001

(54) DERIVATIVE OF CARDANOL AND USES THEREFOR

(75) Inventors: Zhisheng Dai; Meng J. Chen, both of Edison, NJ (US)

(73) Assignee: Cardolite Corporation, Newark, NJ (US)

( * ) Notice: Subject to any disclaimer, the term of this patent is extended or adjusted under 35 U.S.C. 154(b) by 0 days.

(21) Appl. No.: 09/458,229

(22) Filed: Dec. 9, 1999

Related U.S. Application Data

(60) Provisional application No. 60/111,750, filed on Dec. 10, 1998.

(51) Int. Cl.[7] ............................................. C07C 41/00
(52) U.S. Cl. ........................ 568/630; 568/629; 568/648
(58) Field of Search ................................. 568/629, 648, 568/630

(56) References Cited

U.S. PATENT DOCUMENTS

| | | |
|---|---|---|
| 2,434,797 * | 1/1948 | Harvey .................. 568/629 |
| 2,448,767 | 9/1948 | Carlson . |
| 2,967,892 | 6/1961 | Smith . |
| 2,987,555 | 6/1961 | Davis . |
| 3,046,226 * | 7/1962 | Sandberg . |
| 3,214,406 | 10/1965 | Sandberg . |
| 3,283,030 * | 11/1966 | Bean et al. .............. 568/630 |
| 3,644,534 | 2/1972 | Reabe . |
| 4,310,706 * | 1/1982 | Strege . |
| 5,059,723 | 10/1991 | Dressler . |
| 5,068,460 | 11/1991 | Sumner . |
| 5,525,201 | 6/1996 | Diaz-Arauzo . |

FOREIGN PATENT DOCUMENTS

| | | |
|---|---|---|
| 828496 | 2/1960 | (GB) . |
| 2262525 | 6/1993 | (GB) . |

\* cited by examiner

*Primary Examiner*—Deborah D. Carr
(74) *Attorney, Agent, or Firm*—Allen N. Friedman; McCarter & English, LLP

(57) ABSTRACT

The present invention comprises a process for the hydroxyalkylation of cardanol with cyclic organic carbonates in the presence of organic or inorganic catalysts and a novel composition of matter produced by that process. The unique molecular structure of cardanol allows the use of a variety of organic or inorganic basic catalysts, including triethylamine, imidazol, sodium hydroxide and sodium carbonate, in the hydroxyalkylation reaction without forming quantities of undesirable side-products. According to this invention, the final product, monohydroxyalkylcardanyl ether, can be obtained with high yield and high purity. The product has a light color and its color stability is enhanced by replacing the phenol's hydroxyl group with a more stable hydroxyalkoxyl group.

8 Claims, 1 Drawing Sheet

DERIVATIVE OF CARDANOL AND USES THEREFOR

RELATED APPLICATIONS

This application claims priority from Provisional Application Ser. No. 60/111,750 filed on Dec. 10, 1998.

BACKGROUND OF THE INVENTION

1. Field Of The Invention

The invention is in the field of phenol chemistry.

2. Description Of The Background Art

The disclosed novel compound is derived from cardanol, a product obtained by treating cashew nut shell liquid (CNSL). CNSL consists primarily of anacardic acid which is decarboxylated when heated in the presence of acid, giving the meta-substituted phenol, cardanol, used in this invention. (See FIG. 1). Without further refining the resulting product contains a minor amount of a related compound, cardol. (See FIG. 2).

CNSL derivatives have found many industrial uses in, for example, epoxy curing agents, phenolic resins, surfactants, and emulsion breakers. These surfactant-emulsification compounds are oxalkylated to increase their molecular weight and modify their solubility or hydrophilic/lipophilic balance. For example a British patent GB 2,262,525 discloses ethoxylating cardanol with ethylene oxide to form a family of compounds of the formula $C_{15}H_{31-2x}C_6H_4O(C_2H_4O)_nH$, where n is 3 or more, to produce the desired surface-active properties in which there is a balance between the hydrophilic and lipophilic ends of the molecule.

U.S. Pat. No. 2,448,767 disclosed a method of hydroxyethylation wherein ethylene carbonate or ethylene sulfite was reacted with phenols or other active hydrogencontaining compounds, such as thiophenols, amines, alcohols, thioalkohols, and carboxylic acids. The disclosed catalysts included an acid (concentrated sulfuric acid or an alkyl ether of sulfuric acid), a base (alkali carbonates), or the alkali salt of a phenol.

U.S. Pat. No. 2,967,892 disclosed that alkali metal hydroxides were effective catalysts in the hydroxyalkylation reactions of chloromethylethylene carbonate with phenols. U.S. Pat. No. 2,987,555 disclosed that alkali metal hydrides were effective catalysts in the hydroxyalkylation reactions of ethylene carbonate with phenols.

U.S. Pat. No. 4,310,706 disclosed the use of imidazole and its derivatives as catalysts for the reaction of phenols or thiophenols and cyclic organic carbonate compounds with high yields and good monohydroxyalkylation selectivity.

These prior art processes have not been used with cardanol before. Because of the unique molecular structure of cardanol (a long unsaturated side alkyl chain on the benzene ring), the principles disclosed in the prior art processes do not apply in the case of cardanol. For example, these teachings would imply that the use of basic catalysts could produce a significant amount undesirable by-product of secondary reactions between the hydroxyalkylphenyl ether and the carbonate reactant.

SUMMARY OF THE INVENTION

The present invention comprises a process for the hydroxyalkylation of cardanol with cyclic organic carbonates in the presence of organic or inorganic catalysts and a novel composition of matter produced by that process. The unique molecular structure of cardanol allows the use of a variety of organic or inorganic basic catalysts, including triethylamine, imidazole, sodium hydroxide and sodium carbonate, in the hydroxyalkylation reaction without forming quantities of undesirable side-products. According to this invention, the final product, monohydroxyalkylcardanyl ether, can be obtained with high yield and high purity. The product has a light color and its color stability is enhanced by replacing the phenol's hydroxyl group with a more stable hydroxyalkoxyl group.

The novel compound disclosed here is produced by hydroxyalkylating cardol with the cyclic organic carbonates (ethylene carbonate or propylene carbonate) by heating the constituents in the presence of a catalyst. This reaction produces the novel compound having the formula

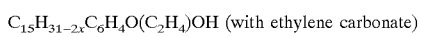
$C_{15}H_{31-2x}C_6H_4O(C_2H_4)OH$ (with ethylene carbonate)

(See FIG. 3.)or

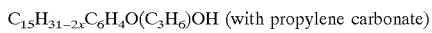
$C_{15}H_{31-2x}C_6H_4O(C_3H_6)OH$ (with propylene carbonate)

(See FIG. 4.), where x is 1, or 2 depending on the number of double bonds in the meta-substituted aliphatic side chain. Carbon dioxide is evolved in the process.

The product is a useful constituent as a modifier in coatings, adhesives, sealants, rubbers, plastics, elastomers, composites and ink because it is a high boiling point, low viscosity liquid whose benzene ring and long side chain structure makes it compatible with many different resins such as alkyds, urethanes, and acrylics. It is an effective constituent of epoxy curing agents. Its high boiling point makes it a stable plasticizer, lending flexibility to, for example, solvent-free epoxy anticorrosive coatings. As a coating constituent it is very light in color and more color stable than other cardanol compounds. Its high boiling point and long chain structure, with one or more unsaturated bonds, produces a plasticizer with good leaching stability. The compound's stability is enhanced by replacement of the phenol's hydroxyl group with a more stable hydroxyl group. This replacement produces greater color stability and reduces the potential for producing contact dermatitis.

DETAILED DESCRIPTION OF THE INVENTION

Figure 1:
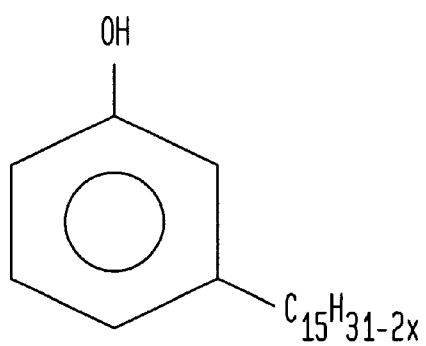
FIG. 1 is a structural diagram of cardanol.
Figure 2:
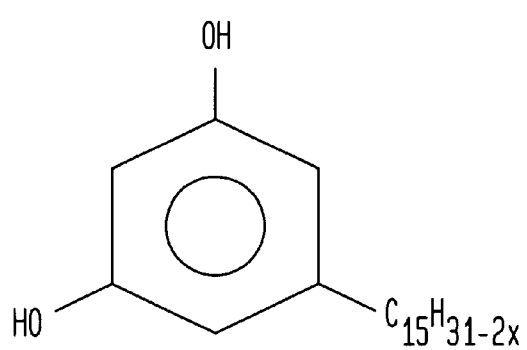
FIG. 2 is a structural diagram of cardol.

The disclosed novel compound is derived from cardanol, a product obtained by treating cashew nut shell liquid (CNSL). CNSL consists primarily of anacardic acid which is decarboxylated when heated in the presence of acid, giving cardanol, a meta-substituted phenol, used in this invention. Without further refining, the resulting product contains a minor amount of a related compound, cardol (See FIG. 2).

The novel compound disclosed here is produced by hydroxyalkylating cardanol with cyclic organic carbonates by heating the constituents in the presence of a catalyst. This reaction produces the novel compound having the formula

$C_{15}H_{31-2x}C_6H_4O(C_2H_4)OH$ (with ethylene carbonate)

Figure 3:
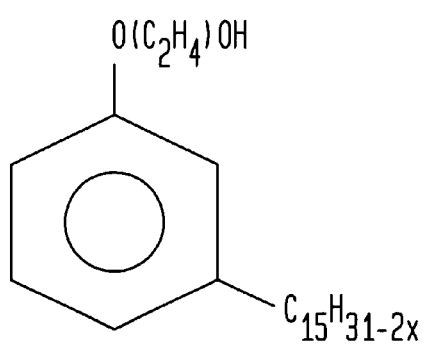
FIG. 3 is a structural diagram of the ethelyne-substituted monohydroxyalkylcardanyl ether.

(See FIG. 3) or

 (with propylene carbonate)

Figure 4:
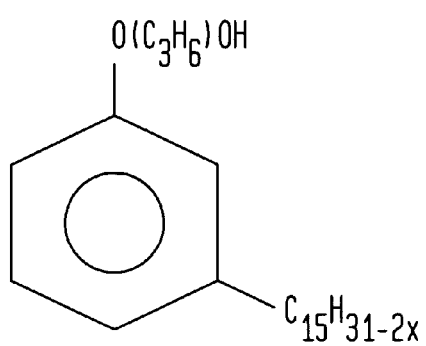
FIG. 4 is a structural diagram of the propylene-substituted monohydroxyalkylcardanyl ether.

(See FIG. 4), where x is 1, or 2 depending on the number of double bonds in the meta-substituted aliphatic side chain. Carbon dioxide is evolved during the process.

The catalysts which may be used in this invention include organic or inorganic bases, such as triethylamine, imidazole or 2-alkyl substituted imidazole, alkali metal hydroxides and alkali metal carbonates. According to this invention, the amount of the catalyst required to make the reaction successful may vary from 0.1 percent to 10.0 percent based on the total reactant weight depending on the specific reaction system. For the two organic catalysts (triethylamine and imidazole or 2-alkyl substituted imidazole), the preferred amount is from 0.2 percent to 2.0 percent; while for the two inorganic catalysts (alkali metal hydroxides and alkali metal carbonates), the preferred amount is 0.5 percent to 5.0 percent. When the inorganic catalysts are employed, water washing is often adopted to get rid of the residual strong base in the product. Mixed catalysts also may be used in this invention.

The cyclic organic carbonates used in this invention may be either ethylene carbonate or propylene carbonate or their mixture. At room temperature, ethylene carbonate is a solid (M. P. 37 C.–39° C.) and it needs to be warmed above its melting point, but it has a higher reactivity in this synthesis. Propylene carbonate is a liquid at room temperature (M. P.–48.7° C.) and it may be directly added to the reaction, but it has a lower reactivity in this synthesis. Also, the product made from propylene carbonate is more hydrophobic than the product made from ethylene carbonate.

The reaction temperature should be controlled between 120° C. to 200° C. according to this invention, and the preferred temperature for ethylene carbonate reaction is 140° C. to 160° C. and for propylene carbonate reaction, from 160° C. to 180° C. Higher reaction temperature may shorten the reaction time but cause product decomposition and by-product formation as well as more violent releasing of carbon dioxide.

The reaction may often be finished in 0.5 hour to 5.0 hours after all the reactants are mixed together. Weakening carbon dioxide releasing is a sign of being close to the end of the reaction. Prolonged reactions may cause product decomposition and by-product formation.

The reaction may be run in high boiling solvents, but the preferred reaction according to this invention does not need any solvent.

According to this invention, the molar ratio of the cardanol to the cyclic organic carbonate may vary from 1:1 to 1:5, and the preferred molar ratio of the cardanol to the cyclic organic carbonate may be from 1.0:1.2 to 1.0:3.0. For the more effective catalysts (imidazole and triethylamine) and/or for the more reactive cyclic organic carbonate (ethylene carbonate), a less amount of cyclic organic carbonate may be charged. The final product may be recovered by distillation or filtration.

EXAMPLES

The following examples are only illustrative examples and they are not to be considered as the limitation of this invention.

Example 1

176 grams of ethylene carbonate (2.0 moles, preheated to 60° C.) and 1.47 grams of triethylamine were added to 300 grams of cardanol (1.0 mole) in a glass flask and the mixture was stirred for approximately 10 minutes. The flask was heated to 150° C. while stirring continued. The mixture bubbled (primarily evolution of $CO_2$,) and its color changed from red to yellow. This process took one hour to 2 hours. The reaction product was then vacuum distilled at 130° C. to 140° C. to remove the unreacted ethylene carbonate. The final product was recovered after filtration.

Results: yield≧95%; monohydroxyethylated ether≧95%, dihydroxyethylated ether<4%, unreacted cardanol<1%, viscosity at 25° C.<100 centipoise, and boiling point at about 230° C. at 2.0 mm Hg.

Example 2

96.8 grams of ethylene carbonate (1.1 moles, preheated to 60° C.) and 2.0 grams of 2-methylimidazole were added to 300 grams of cardanol (1.0 mole) in a glass flask and the mixture was stirred for approximately 10 minutes. The flask was heated to 160° C. and the reaction mixture began to bubble violently. After the reaction was conducted under agitation at 160° C. for 2 hours, the coarse product was distilled under vacuum at 215–220° C. and 300 grams of light yellow distillate were collected (44.6 grams of coarse product still in the flask).

Results from the distillate: yield 87.3%; monohydroxyethylated ether 98.65%, dihydroxyethylated ether 0.92%, and unreacted cardanol 0.43%.

Example 3

107.1 grams of propylene carbonate (1.05 moles, liquid) and 2.0 grams of 2-methylimidazole were added to 300 grams of cardanol (1.0 mole) in a glass flask. Under agitation, the reaction mixture was first heated to 160° C. and kept at 160° C. for 1 hour, then heated to 170° C. and kept at 170° C. for 2 hours, and finally heated to 180° C. and kept at 180° C. for 0.5 hour. The reaction mixture was distilled under vacuum at 230° C., and 344.9 grams of light yellow product were collected.

Results: yield 96.3%; monohydroxyethylated ether 98.86%, dihydroxyethylated ether 0.0%, unreacted cardanol 1.14%, and viscosity at 25° C. 76 centipoise.

Example 4

264 grams of ethylene carbonate (3.0 moles, preheated to 60° C.) and 28.2 grams of sodium carbonate monohydrate were added to 300 grams of cardanol (1.0 mole) in a glass flask. Under agitation, the reaction mixture was heated to 160° C. and kept at 160° C. for 1.5 hours. After the sodium carbonate monohydrate was removed with filtration, 478.7 grams of the reaction mixture were vacuum distilled and 152 grams of the excessive unreacted ethylene carbonate were recovered. After filtration of the liquid remaining in the flask, 326.7 grams of yellow product were obtained.

Results: yield 94.97%; monohydroxyethylated ether 96.58%, dihydroxyethylated ether 2.13%, and unreacted cardanol 1.29%.

Example 5

96.8 grams of ethylene carbonate (1.1 moles, preheated to 60° C. and 2.0 grams of sodium hydroxide pellets were added to 300 grams of cardanol (1.0 mole) in a glass flask. Under agitation, the reaction mixture was heated to 170° C. and kept at 170° C. for 6.0 hours. After the reaction was cooled down to 70° C., the reaction mixture was washed twice with 100 grams of water. Each time, the separation was done at 90° C. and the remaining unreacted ethylene carbonate was gone with the water. The upper layer was vacuum distilled under 100° C. to get rid of the residual water. After filtration of the product in the flask, 307.2 grams of yellow product were collected.

Results: yield 89.3%; monohydroethylated ether 97.4%, dihydroethylated ether 0.81%, unreacted cardanol 1.79%, and viscosity at 25° C. 78.6 centipoise.

What is claimed is:

1. A method for the hydroxyalkylation of cardanol comprising:

a) combining cardanol, a catalyst and at least one cyclic organic carbonate selected from ethylene carbonate and propylene carbonate as reactants;

b) heating the reactants to a reaction temperature and maintaining the combination at the reaction temperature for a reaction time to produce a reaction product; and c) separating the reaction product from uncombined reactants, whereby the reaction product consists essentially of a monohydroxyalkylcardanyl ether, wherein the catalyst is 2-methylimidazole, sodium hydroxide or sodium carbonate.

2. A method of claim 1 in which the catalyst is included in the reactants in an amount from 0.1 weight percent to 10 weight percent of the total weight of reactants.

3. A method of claim 1 in which the reaction temperature is from 120° C. to 220° C.

4. A method of claim 1 in which the reaction time is from 1 hour to 5 hours.

5. A method of claim 1 in which the molar ratio of the cardanol constituent to the carbonate constituent is from 1:1 to 1:5.

6. A method of claim 1 in which the reaction product is separated by vacuum distillation or filtering, or a combination of distillation and filtering.

7. A composition of matter consisting essentially of a monohydroxyalkylcardanyl ether of the formula of $C_{15}H_{31-2x}C_6H_4O(C_2H_4)OH$, where x is 1, or 2, represented by the following structure:

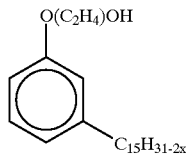

8. A composition of matter consisting essentially of a monohydroxyalkylcardanyl ether of the formula, $C_{15}H_{31-2x}C_6H_4O(C_3H_6)OH$, where x is 1, or 2, represented by the following structure:

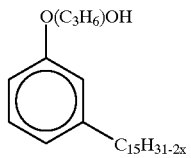

* * * * *

UNITED STATES PATENT AND TRADEMARK OFFICE
CERTIFICATE OF CORRECTION

PATENT NO.   : 6,229,054 B1
DATED        : May 8, 2001
INVENTOR(S)  : Zhisheng Dai; Meng J. Chen Page 1 of 1

It is certified that error appears in the above-identified patent and that said Letters Patent is hereby corrected as shown below:

Column 2,
Line 11, delete "cardol" and insert -- cardanol --.
Line 46, delete "ethelyne" and insert -- ethylene --.

Column 4,
Line 61, after "1.1 moles" insert -- ) --.

Signed and Sealed this

Fifth Day of March, 2002

Attest:

Attesting Officer

JAMES E. ROGAN
Director of the United States Patent and Trademark Office